(12) United States Patent
Anderson

(10) Patent No.: US 6,358,254 B1
(45) Date of Patent: Mar. 19, 2002

(54) METHOD AND IMPLANT FOR EXPANDING A SPINAL CANAL

(75) Inventor: D. Greg Anderson, The Benjamin Franklin House, #1424, 834 Chestnut St., Philadelphia, PA (US) 19107

(73) Assignee: D. Greg Anderson, Charlottesville, VA (US)

( * ) Notice: Subject to any disclaimer, the term of this patent is extended or adjusted under 35 U.S.C. 154(b) by 0 days.

(21) Appl. No.: 09/659,180

(22) Filed: Sep. 11, 2000

(51) Int. Cl.[7] .............................................. A61B 17/70
(52) U.S. Cl. ...................... 606/103; 606/61; 623/17.11
(58) Field of Search ........................... 606/61, 74, 103; 623/17.11, 17.16

(56) References Cited

U.S. PATENT DOCUMENTS

| | | | | |
|---|---|---|---|---|
| 4,917,704 A | * | 4/1990 | Frex et al. ...................... | 606/61 |
| 4,955,908 A | * | 9/1990 | Frex et al. ...................... | 606/61 |
| 5,059,193 A | | 10/1991 | Kuslich ........................ | 606/61 |
| 5,176,678 A | | 1/1993 | Tsou ............................. | 606/61 |
| 5,258,031 A | * | 11/1993 | Salib et al. .................... | 606/61 |
| 5,425,772 A | * | 6/1995 | Brantigan ..................... | 606/61 |
| 5,480,440 A | | 1/1996 | Kambin ........................ | 623/17 |
| 5,496,322 A | | 3/1996 | Mathews ..................... | 606/61 |
| 5,653,762 A | * | 8/1997 | Pisharodi ..................... | 606/61 |
| 5,653,763 A | | 8/1997 | Errico et al. .................. | 623/17 |
| 5,722,977 A | * | 3/1998 | Wilhelmy ..................... | 606/61 |
| 5,725,527 A | | 3/1998 | Biedermann et al. ......... | 606/61 |
| 5,766,251 A | * | 6/1998 | Koshino ....................... | 606/61 |
| 5,772,663 A | * | 6/1998 | Whiteside .................... | 606/74 |
| 5,836,948 A | | 11/1998 | Zucherman et al. .......... | 606/61 |
| 6,008,433 A | * | 12/1999 | Stone ........................... | 606/61 |
| 6,077,268 A | * | 6/2000 | Farris et al. ................. | 606/103 |
| 6,099,531 A | * | 8/2000 | Bonutti .................... | 623/17.16 |
| 6,224,599 B1 | * | 5/2001 | Baxnham et al. ............. | 606/61 |
| 6,248,106 B1 | * | 6/2001 | Ferrel .......................... | 606/61 |

\* cited by examiner

*Primary Examiner*—Paul J. Hirsch
(74) *Attorney, Agent, or Firm*—Saul Ewing LLP

(57) ABSTRACT

The present invention expands a spinal canal by making two pedicle cuts (osteotomies) in a vertebra, separating each vertebral cut by inserting an implant into the cut which expands the spinal canal, and securing each separated vertebral cut allowing the vertebra to heal with the spinal canal expanded. The implant includes two stents, two washers, two screws and a cable. One stent is impacted into each pedicle cut in the vertebra. One screw is inserted through one washer and one stent and is threaded into an anterior portion of the vertebra for each pedicle cut in the vertebra. The cable is attached at each end to a washer and is strapped around and through a posterior portion of the vertebra to secure the posterior portion of the vertebra to the anterior portion of the vertebra, stabilizing the expanded spinal canal and allowing the vertebra to heal with the spinal canal expanded.

26 Claims, 6 Drawing Sheets

METHOD AND IMPLANT FOR EXPANDING A SPINAL CANAL

BRIEF OF THE INVENTION

The present invention relates generally to spinal surgery, and more particularly to a method and apparatus for expanding a spinal canal to relieve pressure on spinal nerves.

BACKGROUND OF THE INVENTION

Spinal Stenosis, or narrowing of the spinal canal, inflicts millions of people with back and leg pain due to compression of spinal nerves. Severe spinal stenosis often leads to surgery in an effort to relieve compressed nerves and lessen back and leg pain. Spinal laminectomy is the traditional operation performed to treat spinal stenosis. In the spinal laminectomy, posterior aspects of the spinal column are removed to "un-roof" the spinal canal to relieve the pressure on the nerves. Specifically, a spinous process, lamina and portions of various facet joints are the posterior aspects of the spinal column surgically excised.

Although the spinal laminectomy is often successful in relieving pressure on the nerves of the spinal canal, several problems and disadvantages arise as a result of the laminectomy. First, the laminectomy removes important sites of back muscle attachment leading to back muscle dysfunction and pain. Second, the laminectomy exposes the nerve sac causing scar tissue to form around the nerves. Scar tissue may prevent normal motion of the nerves, leading to recurrent pain. Third, the laminectomy can destabilize the spine resulting in a forward slippage of one vertebra on another. Vertebral slippage can cause recurrent pain and deformity. Fourth, the laminectomy requires a large surgical exposure and significant blood loss, making the laminectomy dangerous for older patients. Finally, spinal stenosis can recur following the laminectomy, requiring risky revision surgery.

Laminectomy risks have led surgeons to seek an alternative for patients with severe spinal stenosis. Some surgeons choose to treat spinal stenosis with multiple laminotomies. Laminotomies involve removing bone and soft tissue from the posterior aspect of the spine making "windows" into the spinal canal over areas of nerve compression. Multiple laminotomies remove less tissue than the laminectomy, resulting in less scaring, vertebral instability and blood loss.

Multiple laminotomies, however, also suffer from problems and disadvantages. Laminotomies may not adequately relieve nerve compression and the pain may continue. Laminotomies are more difficult to correctly perform than the laminectomy. Laminotomies expose the nerves and may cause nerve scaring. Patients receiving multiple laminotomies also often have recurrent spinal stenosis requiring risky revision surgery.

Zucherman, et. al., discloses another approach (differing from laminectomies, laminotomies and the present invention) to spinal stenosis in U.S. Pat. No. 5,836,948, where a device and method is described to distract (spread apart) spinous processes of adjacent vertebrae and prevent extension of the spine. While the Zucherman technique may help to relieve some spinal canal narrowing due to in folding of posterior soft tissues, the bony spinal canal remains unchanged in size. Without expanding the spinal canal area, the Zucherman technique offers limited benefit for spinal stenosis sufferers. Furthermore, arthritic facet spurs, the main cause of degenerative spinal stenosis, remain unaffected by the Zucherman approach and continue to cause pain. Also, the distraction of the spinous processes as described by Zucherman creates a forward curvature of the spine called kyphosis. Lumbar kyphosis is a spinal deformity often associated with back pain and dysfunction.

Information relevant to a wide variety of spinal implants including screw and rod constructs are described by Biedermann et. al. in U.S. Pat. No. 5,725,527, Tsou in U.S. Pat. No. 5,176,678, Kambin in U.S. Pat. No. 5,480,440 and Mathews in U.S. Pat. No. 5,496,322. These implants are useful for stabilizing the spine and the correcting spinal deformities, however, these references are not capable of expanding the spinal canal or treating spinal stenosis. Other implants operating as intervertebral spacers are described by Errico et. al in U.S. Pat. No. 5,653,763 and Kuslich in U.S. Pat. No. 5,059,13. These implants are useful in expanding the intervertebral disc space and assisting with spinal fusion, however, these references are also not capable of expanding the spinal canal or treating spinal stenosis.

For the foregoing reasons, there is a strong need for a different and better method for relieving the symptoms of spinal stenosis without the drawbacks of currently available techniques. A method is needed that expands the spinal canal, relieving pressure on the spinal nerves, while being simple, safe and permanent.

SUMMARY OF THE INVENTION

The present invention provides a simple, safe and permanent method and apparatus for treating spinal stenosis by expanding the spinal canal area to provide additional space for the spinal nerves, relieving pressure on the spinal nerves.

An object of the present invention is to maintain the integrity of the spinal canal so that the function of normal tissues is not destroyed or significantly altered as with a larninectomy and laminotomy.

Another object of the present invention is to avoid scarring around the spinal nerves by avoiding an open exposure of the nerves.

Another object of the present invention is to avoid causing spinal instability, where one vertebra slips forward on another vertebra causing recurrent pain and deformity.

Yet another object of the present invention is to decompress the spinal nerves with a quick, safe approach resulting in minimal blood loss.

Yet another object of the present invention is to provide a permanent solution to spinal stenosis, where no tendency exists for recurrence.

In one aspect of the present invention, a method for correcting spinal stenosis is introduced where a spinal canal is enlarged by cutting a vertebra, separating the vertebral cut and then stabilizing the cut, allowing the vertebra to heal with the spinal canal expanded, permanently creating more space for the spinal nerves thus relieving compression on the nerves.

In another aspect of the present invention, the method of expanding the spinal canal begins with cutting a vertebra (performing an osteotomy) at each spinal pedicle of the vertebra in an oblique fashion, beginning at a base of a transverse process of the vertebra and coursing medially and anteriorly at approximately a 45-degree angle to complete the cut through a medial wall of the pedicle to the spinal canal. Each osteotomy (bone cut) is then distracted (expanded) by inserting an implant into the osteotomy, increasing the diameter (and thus the area) of the spinal canal. The implant is stabilized, securing the osteotomies and the vertebra with the spinal canal in an expanded state.

In another aspect of the present invention, the implant comprises a stent and a screw. The stent is inserted into the vertebral cut, expanding the spinal canal. The screw is inserted through the stent and threaded into the vertebra, securing the stent, the vertebral cut and the expanded spinal canal.

In another aspect of the present invention, the implant comprises two stents and two screws. Each stent is inserted into one of two vertebral cuts, each stent insertion expanding the spinal canal. Each screw is inserted through one stent and threaded into the vertebra, securing the stent, the vertebral cut and the expanded spinal canal.

In another aspect of the present invention, the implant includes two stents, two screws, two washers and a cable. Each stent is inserted into one of two vertebral cuts, each stent insertion expanding the spinal canal. Each screw is inserted through one washer and one stent. Each screw is then threaded into an anterior portion of the vertebra, securing the washer, the stent, the vertebral cut and the expanded spinal canal. Each washer is connected to one of two ends of the cable, the cable being strapped around or through a posterior portion of the vertebra, securing the posterior portion of the vertebra to the anterior portion of the vertebra.

In another aspect of the present invention, the screw can include self-tapping, bone gripping threads. The screw can also include a rounded head.

In another aspect of the present invention, the stent is designed to accommodate the insertion of bone graft material to facilitate healing of the vertebra with expanded spinal canal. The stent can be U-shaped for this purpose. The stent can include a rounded, wedge-shaped end for ease in penetrating and separating the vertebral cut. The stent can include a flange designed to prevent the stent from penetrating into the spinal canal. The stent can also include a rounded depression adapted to rotatably accept a rounded washer and/or a rounded head on the screw for securing the stent to the vertebra.

In another aspect of the present invention, the washer can include a rounded shape substantially similar to and engagable with a rounded head on the screw and a rounded depression in the stent. The rounded head of the screw would reside within the rounded washer and both would be rotatably housed within the rounded depression in the stent.

The present invention has the following advantages over current, unrelated techniques for treating spinal stenosis:

(1) Normal spine structures are not removed and thus normal muscle attachments are maintained.
(2) There is less chance of spinal instability.
(3) There is less manipulation of the spinal nerves.
(4) There is less scaring around the spinal nerves.
(5) Spinal decompression is more complete.
(6) The operation is quicker and safer with less blood loss.
(7) The expanded spinal canal is permanent, preventing recurrent spinal stenosis.

BRIEF DESCRIPTION OF THE DRAWINGS

For the purpose of illustrating the invention, there is shown in the drawings a form which is presently preferred; it being understood, however, that this invention is not limited to the precise arrangements and instrumentalities shown.

DETAILED DESCRIPTION OF THE INVENTION

Figure 1:
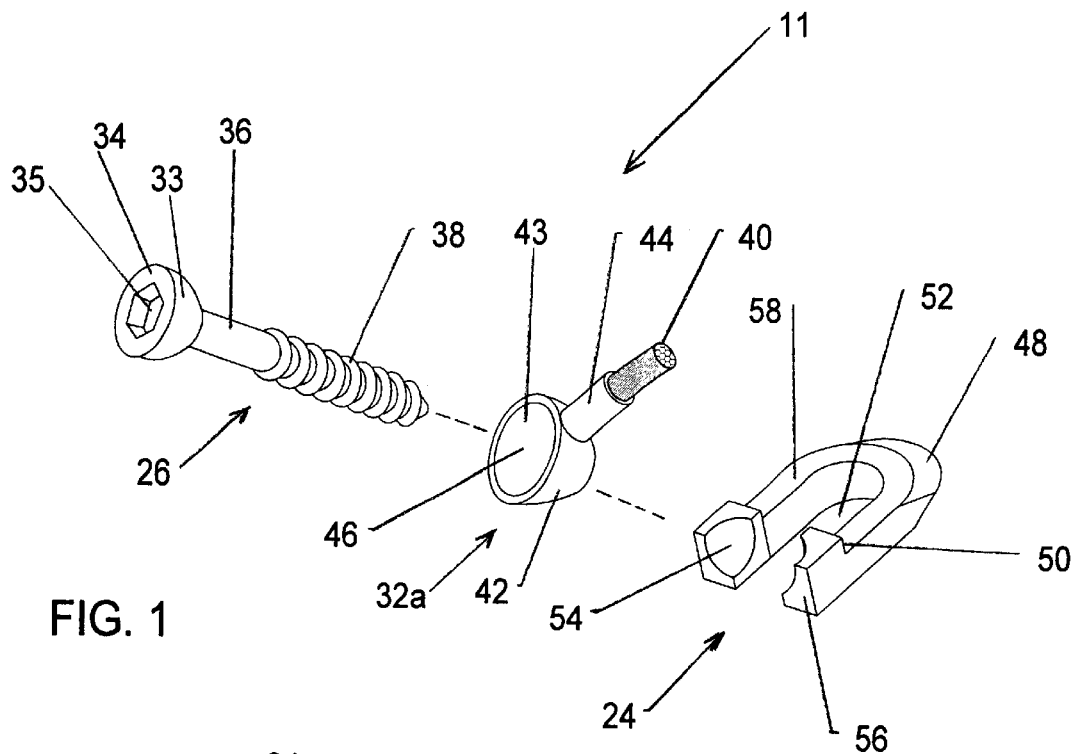
FIG. 1 illustrates an exploded view of an implant comprising a screw, a rounded washer with a cable end-attachment and a stent, in accordance with the present invention.

Referring now to the drawings, wherein like numerals indicate like elements, there is shown in FIG. 1 an exploded view of an implant 11 comprising a screw 26, a rounded washer with end-attachment 32a, a cable 40 and a stent 24. The stent 24 is designed for impaction into a vertebral osteotomy (bone cut), to expand the sides of the osteotomy apart. Once in place, the stent 24 is designed to contain bone graft material to assist the healing of the osteotomy.

The stent 24 has a rounded, wedge shaped end 48, a U-shaped sidewall 58 and an expanded end 56. There is a flange 50 at the juncture of the expanded end 56 and the U-shaped sidewall 58. The expanded end 56 contains a rounded depression 54 to accept the screw 26 and/or the rounded washer 32a. The rounded, wedge-shaped end 48 is designed to enter and wedge apart the sides of the osteotomy. The U-shaped sidewall 58 surrounds an interior section 52 of the stent 24 which can be filled with bone graft after the impaction of the stent 24 into the osteotomy.

The screw 26 includes a head 34 having a screwdriver socket 35 and a rounded outer surface 33. The rounded outer surface 33 is adapted to engage an inner surface 43 of the rounded washer 32a. The screw 26 also includes a shank 36 with threads 38 designed to grip vertebral bone and can be the self-tapping variety.

The rounded washer with end-attachment 32a includes a central passage 46 for the screw 26 and an inner surface 43 adapted to accept the outer surface 33 of the screw head 34. The rounded washer 32a also includes a rounded outer surface 42, adapted to engage the rounded depression 54 of the stent 24 allowing the rounded washer 32a to rotatably reside within the rounded depression 54. The outer surface 42 of the rounded washer 32a has a connector 44 for attaching an end of a cable 40 to the rounded washer 32a.

Figure 4A:
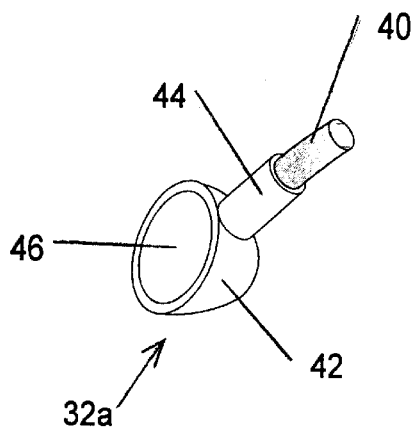
FIG. 4a illustrates a perspective view of the rounded washer as shown in FIG. 1 with the cable end-attachment.
Figure 4B:
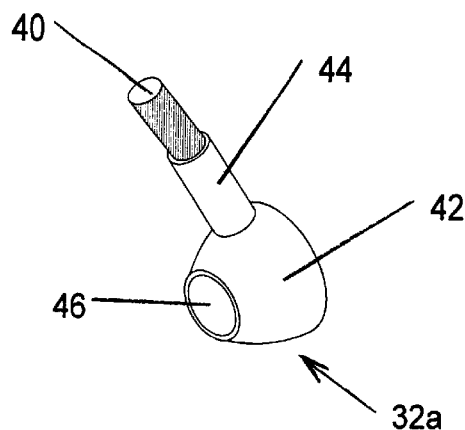
FIG. 4b illustrates an underside perspective view of the rounded washer of FIG. 4a with the cable end-attachment.
Figure 4C:
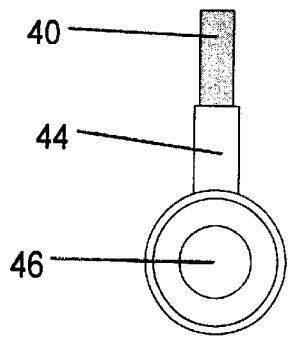
FIG. 4c illustrates a top plan view of the rounded washer of FIG. 4a with the cable end-attachment.
Figure 4D:
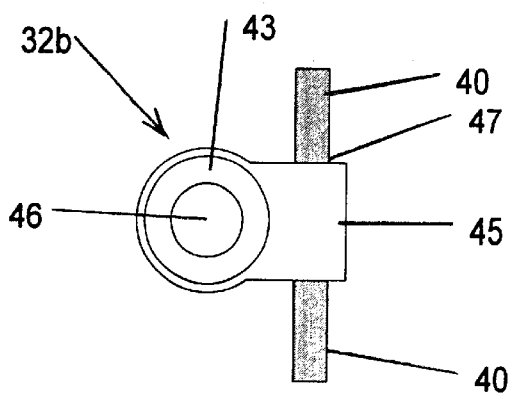
FIG. 4d illustrates a top plan view of a rounded washer with a cable side-attachment, in accordance with the present invention.
Figure 4E:
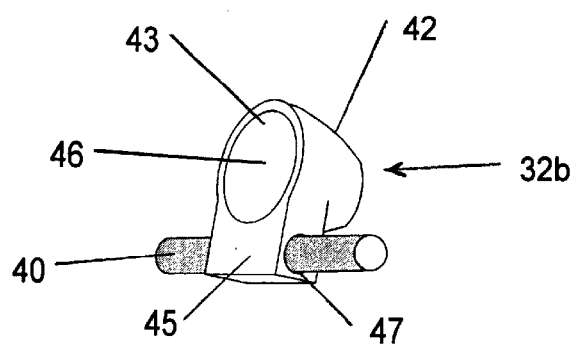
FIG. 4e illustrates a perspective view of the rounded washer of FIG. 4d with the cable side-attachment.

FIGS. 4a through 4e illustrate two embodiments of the rounded washer 32a, 32b. The rounded washer with end-attachment 32a for the cable 40 is shown in FIGS. 4a through 4c. A rounded washer with side-attachment 32b for the cable 40 is shown in FIGS. 4d and 4e. FIG. 4a illustrates a perspective view of the rounded washer with end-attachment 32a as shown in FIG. 1. FIG. 4b illustrates a second perspective view of the rounded washer 32a, showing the central passage 46 from below and the connector 44 for end-attachment of the cable 40. FIG. 4c illustrates a top plan view of the rounded washer 32a, also showing the central passage 46, the connector 44 and the cable 40.

FIGS. 4d and 4e illustrate the rounded washer with side-attachment 32b. The rounded washer with side-attachment 32b has a similarly shaped central passage 46, rounded inner surface 43 and rounded outer surface 42 as the rounded washer with end-attachment 32a. As such, the rounded washer 32b is similarly designed to accept the screw 26 and to rotatably reside within the rounded depression 54 of the stent 24.

The rounded washer with side-attachment 32b differs from the rounded washer with end-attachment 32a only in its cable 40 attachment means, having a side passage 45 with a tunnel 47 slightly larger than the cable 40 so that the cable 40 is slidably movable within the tunnel 47. The slidable movement of the cable 40 through the tunnel 47 allows tensioning of the cable 40 to remove cable slack. The cable 40 may then be secured to the side passage 45 by crushing or plastically deforming the side passage 45 around the cable 40 to firmly hold the cable 40 in place. Alternatively, the side passage 45 could be secured to the cable 40 by other means, such as by setscrew.

Figure 2:
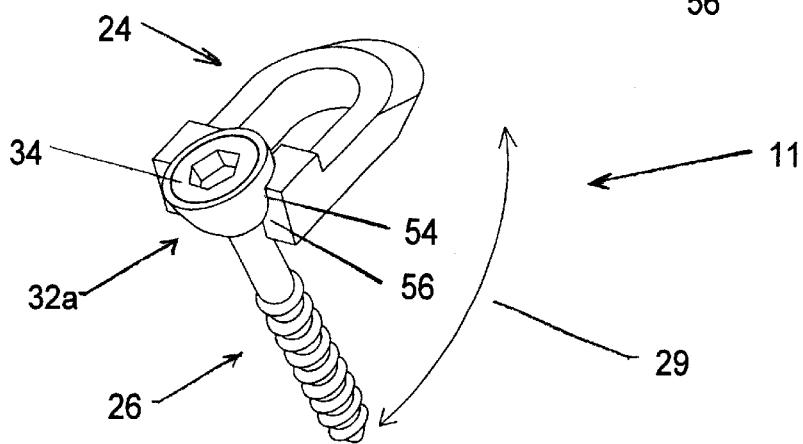
FIG. 2 illustrates a perspective view of the implant of FIG. 1 without the cable end-attachment on the rounded washer, to show the relationship of the screw, the rounded washer and the stent.

FIG. 2 illustrates the screw 26, the rounded washer 32a and the stent 24 engaged together. The connector 44 and the cable 40 (shown in FIG. 1) are removed in FIG. 2 to detail the engagement of the screw 26, the rounded washer 32a and the stent 24. The head 34 of the screw 36 is seated within the rounded washer 32a. The rounded washer 32a is seated within the rounded depression 54 of the expanded end 56 of the stent 24. The shape of the head 34 of the screw 26, the rounded washer 32a and the rounded depression 54, allow the screw 26 and the rounded washer 32a to move or rotate within the rounded depression 54 of the stent 24 (illustrated by the arrow 29). Therefore, the angle between the screw 26 and the stent 24 is variable to assist with accurate placement of the implant 11.

Figure 3:
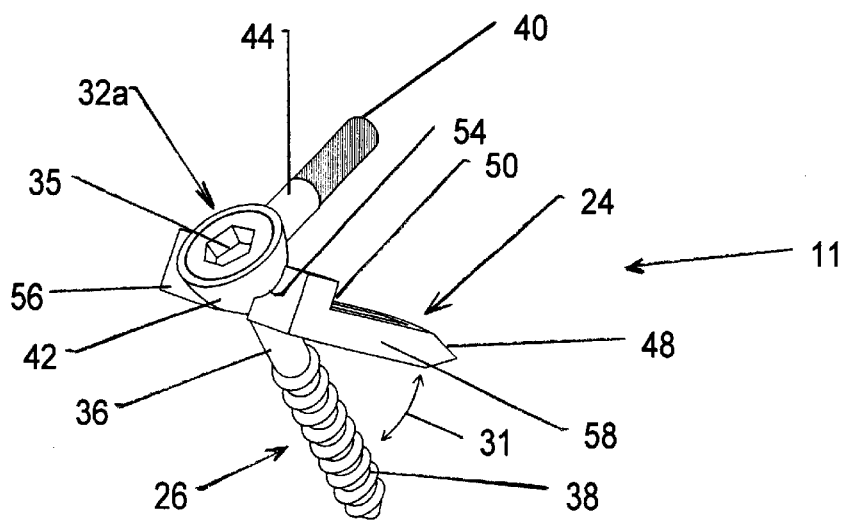
FIG. 3 illustrates a perspective view of the implant of FIG. 1 having an angle between the stent and the screw typical of the implant when inserted into a vertebra.

FIG. 3 illustrates the implant 11 with the screw 26, the rounded washer with end-attachment 32a, the cable 40 and the stent 24 engaged and positionally angled (relative to one another) similar to implant 11 positioning within a vertebra in accordance with the present invention. The screw 26 is seated within the rounded washer 32a, the rounded washer 32a is seated within the rounded depression 54 of the stent 24. The stent 24 and screw 26 form an acute angle 31, positioning the connector 44 and the cable 40 in an upward direction relative to the stent 24.

The implant 11 could be made of materials including but not limited to: stainless steel, titanium alloy, cobalt chromium alloy, bone, polyethylene, and polymers of lactide, glycolide, caprolactone, polydioxanone, trimethylene carbonate, polyorthoesters, polyethelene oxide or blends of the above polymers.

Figure 5:
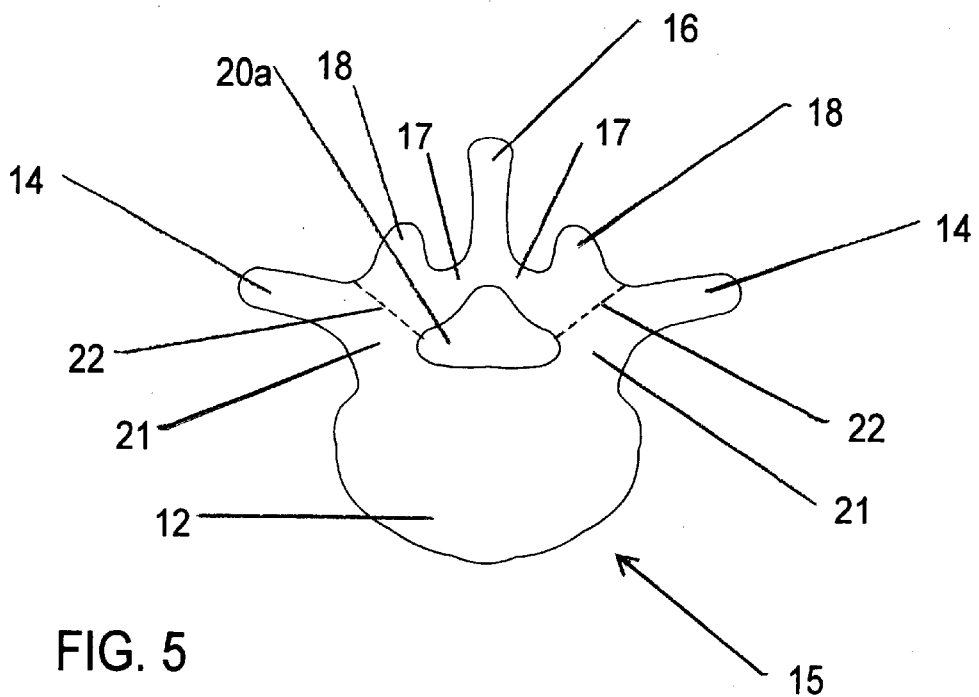
FIG. 5 illustrates a cross-section view of a vertebra, where dashed lines represent locations of vertebral cuts (osteotomies), in accordance with the present invention.

FIG. 5 illustrates a cross-section of a vertebra 15 comprising a vertebral body 12, a pedicle 21, a transverse process 14, a superior articular process 18, a lamina 17, a spinous process 16 and spinal canal (unexpanded) 20a. The dashed lines represent the site of the osteotomies (bone cuts) 22. Each osteotomy 22 begins at the base of the transverse process 14 and courses at approximately a 45-degree angle (relative to a coronal plane) towards a medial wall of the pedicle 21. Cutting the pedicle 21 as described (as shown by the dashed lines) separates a posterior portion of the vertebra (the spinous process 16, the superior articular process 18, and the lamina 17) from an anterior portion of the vertebra (the pedicle 21, the transverse process 14, and the vertebral body 12).

The osteotomy (bone cut) 22 is performed by any commonly known method for cutting bone, such as using a wire saw, a oscillating power saw or an osteotome. Of course, care should be taken to protect the spinal nerves while performing the osteotomy.

Figure 6:
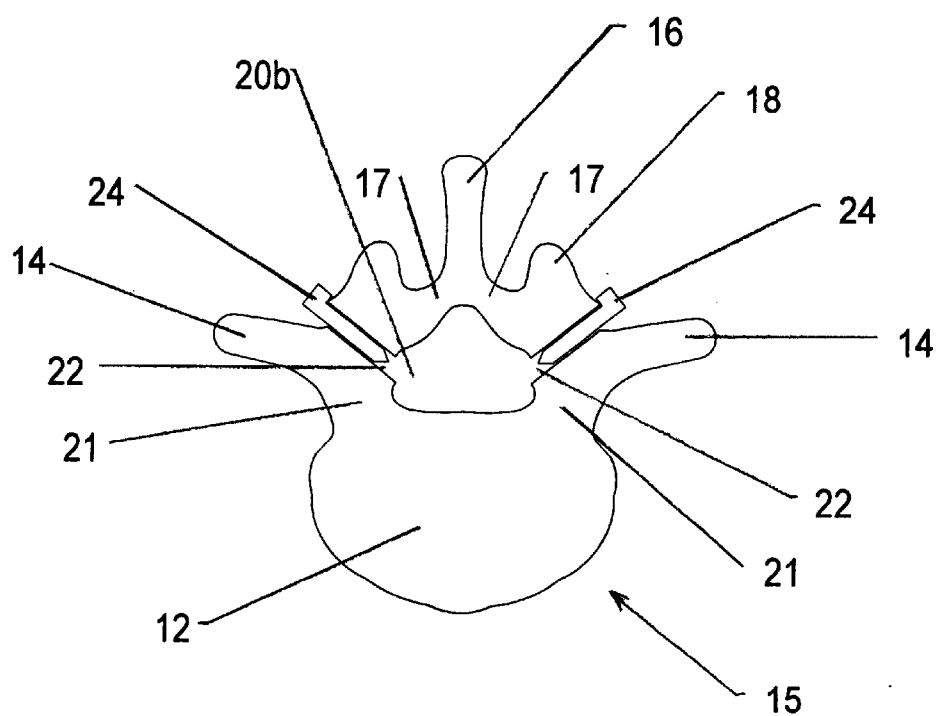
FIG. 6 illustrates a cross-section view of a vertebra after expanding the spinal canal by inserting the stents in the osteotomies, in accordance with the present invention.

FIG. 6 illustrates a cross-section of the vertebra 15 showing an expanded spinal canal 20b. Osteotomies 22 were completed through both pedicles 21 and stents 24 were placed into each osteotomy 22. The stents 24 distract (separate) and hold the edges of the osteotomy 22 apart. Distracting the osteotomies 22 by inserting stents 24 expands the spinal canal 20b, increasing its diameter relative to that of the unexpanded spinal canal 20a shown in FIG. 5.

Figure 7:
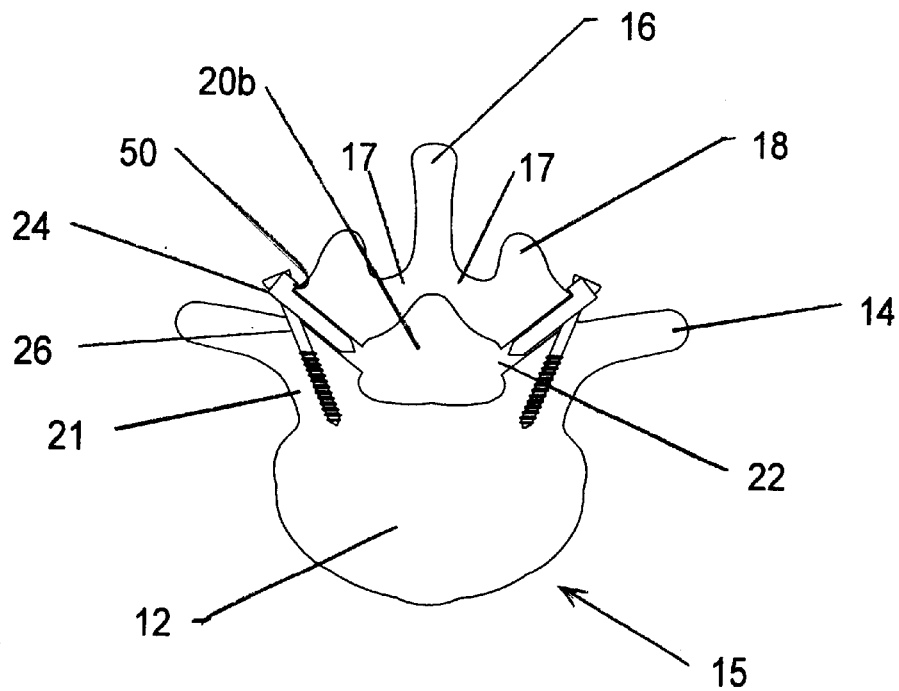
FIG. 7 illustrates a cross-section view of the vertebra of FIG. 6, with screws stabilizing the expanded spinal canal by insertion through the stents and into the vertebra, in accordance with the present invention.

FIG. 7 illustrates a cross-section of the vertebra 15 showing the expanded spinal canal 20b, with a screw 26 threaded into a pedicle 21 to secure the stent 24 inserted into each osteotomy 22. The screws 26 are seated within the rounded depression 54 of the stent 24, preventing the stent 24 from sliding out of the osteotomy 22. The flange 50 on the stent 24 prevents the stent 24 from penetrating the spinal canal 20b, by preventing further movement of the stent 24 into the osteotomy 22.

Prior to placement of each screw 26 into the pedicle 21, bone graft material (not shown) should be placed into the interior section 52 of each stent 24 to assist with healing of the osteotomy 22. The screw 26, the U-shaped sidewall 58 of the stent 24 and the sides of the osteotomy 22 completely contain the bone graft material placed within the interior section 52 of the stent 24, preventing a release of the bone graft material prior to vertebral healing.

The spinous process 16, the lamina 17 and the superior articular process 18 rest on the stent 24 and are held in place (fixed against the stent 24) by surrounding soft tissues. Concluding the procedure in this manner (relying on surrounding soft tissue to secure the posterior portion of the vertebra to the anterior portion) would be appropriate in stiff, arthritic spines where there is no tendency for the vertebrae to slip on one another.

Figure 8:
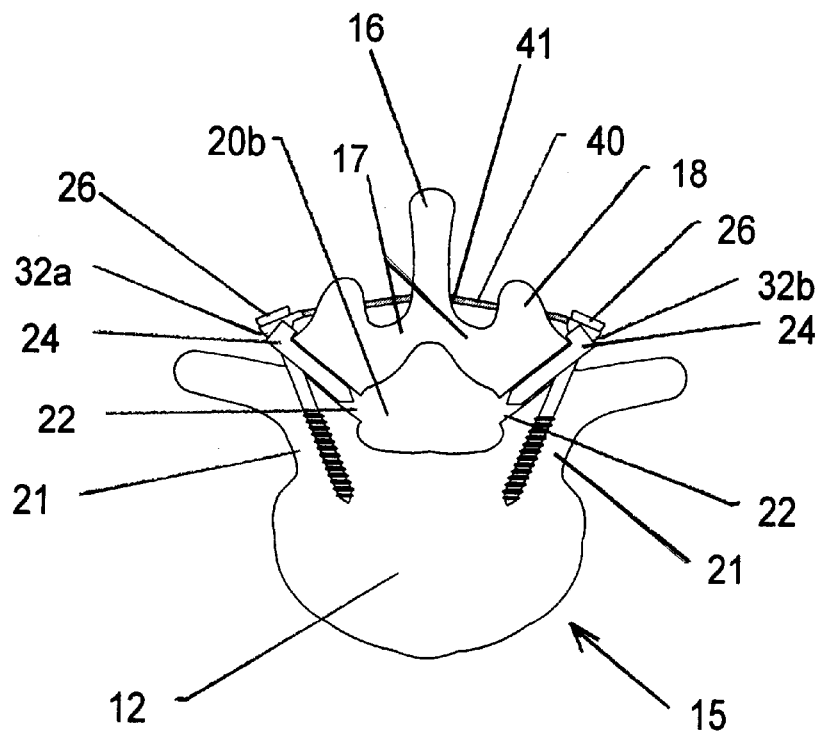
FIG. 8 illustrates a cross-section view of the vertebra of FIG. 7, with the screws, rounded washers and a cable stabilizing the expanded spinal canal, in accordance with the present invention;.

FIG. 8 illustrates a cross-section of the vertebra 15 showing the expanded spinal canal 20b. In addition to the screws 26 threaded into the pedicles 21 to secure the stents 24 in the osteotomies 22, rounded washers 32a, 32b and a cable 40 are added to secure the spinous process 16, the lamina 17 and the superior articular process 18 against the stents 24 for healing of the vertebra 15.

The screws 26 pass through the rounded washers 32a, 32b and are threaded into the bone of the pedicle 21. The cable 40 is secured at each end by attachment to the rounded washers 32a, 32b. First, the rounded washer with end-attachment 32a for the cable 40 (with the cable 40 attached) is mounted into the rounded depression 54 in the stent 24 and the screw 26 is inserted through the rounded washer 32a and threaded into the pedicle 21. Next, the cable 40 is aligned across a top (dorsal) surface of the lamina 17 and inserted through a hole 41 drilled in a base of the spinous process 16. The cable is then aligned across a top (dorsal) surface of the other lamina 17 and is inserted through the tunnel 47 in the side passage 45 of the rounded washer with side-attachment 32b. The cable 40 is tensioned to remove all slack (by pulling the cable 40 taut through the tunnel 47) and the side passage 45 is crushed, plastically deformed or bolted to fixedly connect the cable 40 to the rounded washer 32b, firmly securing the cable 40 between the rounded washers 32a, 32b and the stents 24. Alternatively, two rounded washers with side-attachment 32b could be used, depending on operational conditions and user preference.

The cable 40 secures the spinous process 16, the lamina 17 and the superior articular process 18 (the posterior portions of the vertebra 15) to the pedicle 21 and the vertebral body 12, yielding a mechanically stable spinal canal. The addition of the cable 40 and the rounded washers 32a, 32b lends stability to the osteotomies 22, preventing slippage of the vertebra 15. Again, bone graft material should be placed within the interior section 52 of the stent 24 prior to placement of the screws 26, the rounded washers 32a, 32b and the cable 40.

Figure 9A:
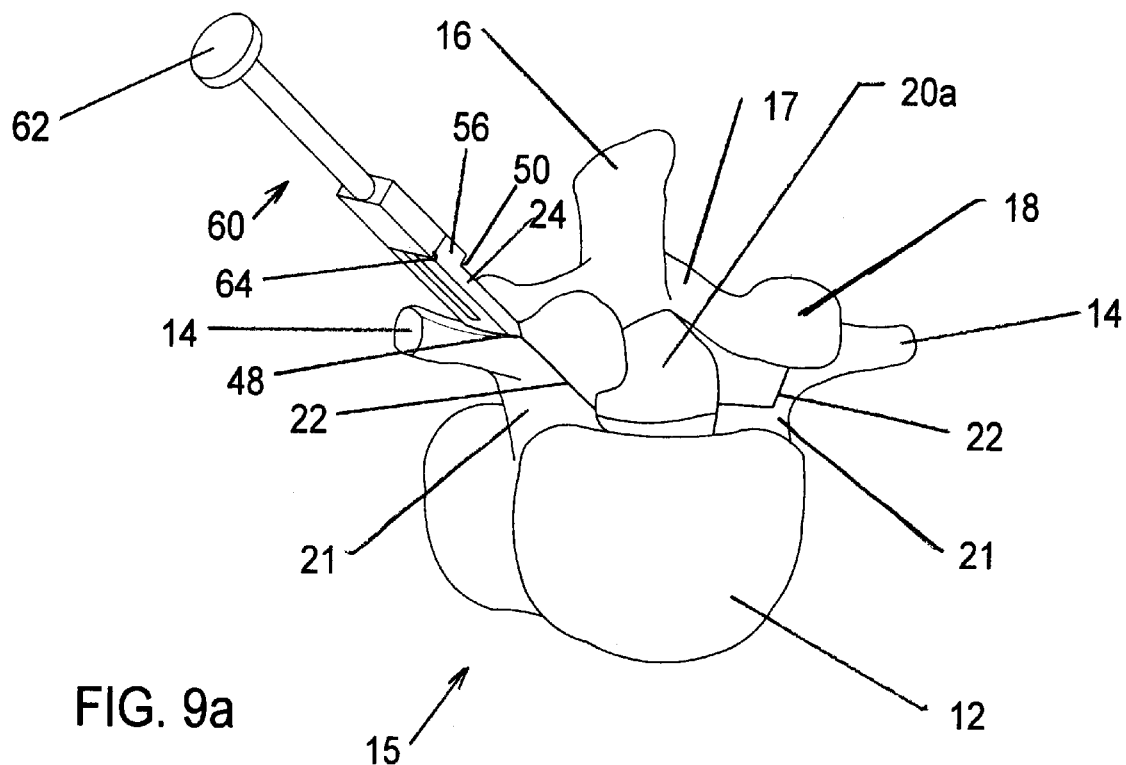
FIG. 9a illustrates a perspective view of a vertebra with pedicle osteotomies in place and a stent ready for impaction into one of the osteotomies, in accordance with the present invention.

FIG. 9a illustrates a perspective view of a vertebra 15 after creation of an osteotomy (bone cut) 22 through each pedicle 21. Each osteotomy 22 extends obliquely from the base of the transverse process 14 through the pedicle 21 to the spinal canal (unexpanded) 20a. The stent 24 is ready for impaction into one of the osteotomies 22. The rounded, wedge-shaped end 48 of the stent 24 is placed at the edge of the osteotomy 22. An impactor 60 having a mallet end 62 and an impact end 64 is placed into contact with the expanded end 56 of the stent 24. The impact end 64 of the impactor 60 is adapted for flush engagement with the expanded end 56 of the stent 24. Mallet blows to the mallet end 62 of the impactor 60 drives the rounded, wedge-shaped end 48 of the stent 24 into the osteotomy 22, causing the osteotomy 22 to wedge open as the stent 24 enters the osteotomy 22. The stent 24 is driven into the osteotomy 22 until the flange 50 contacts the osteotomy 22 edge at the base of the transverse process 14, preventing further movement of the stent 24 into the osteotomy 22. To expand the spinal canal 20a in a symmetric fashion, the opposite osteotomy 22 also receives a stent 24.

Figure 9B:
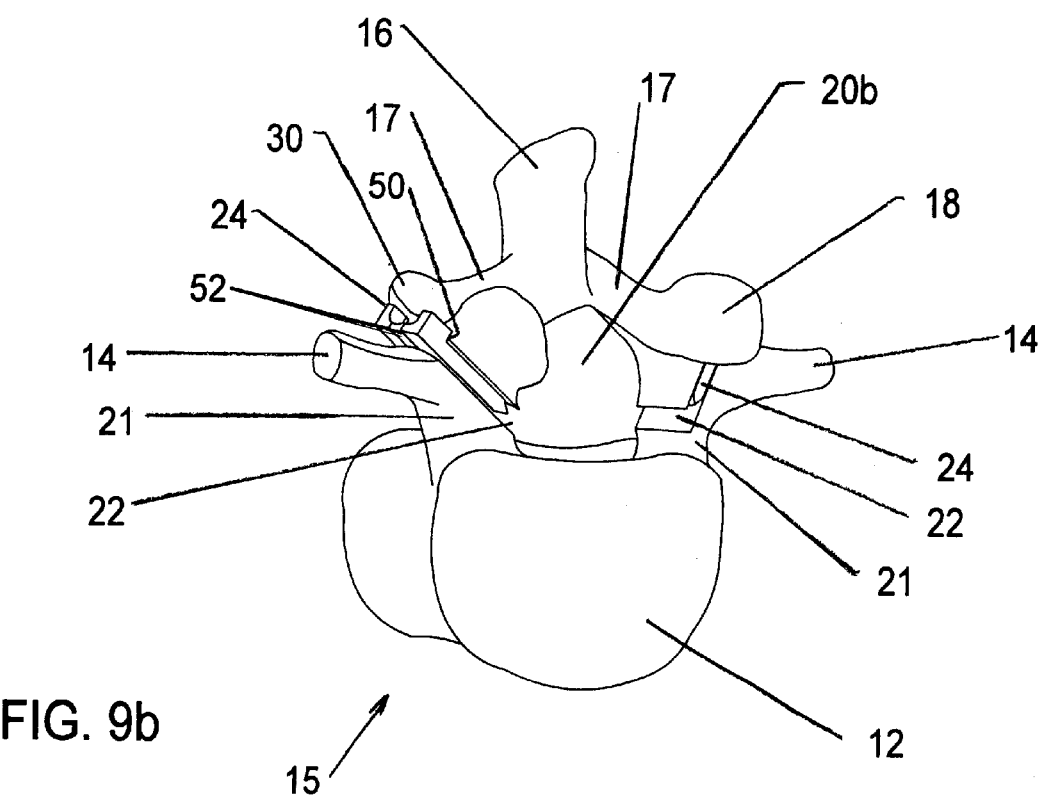
FIG. 9b illustrates a perspective view of the vertebra of FIG. 9a, after expanding the spinal canal by inserting stents in the osteotomies, in accordance with the present invention.

FIG. 9b illustrates the vertebra 15 of FIG. 9a with an expanded spinal canal 20b after placement of the stents 24 into the osteotomies 22. The stents 24 hold the osteotomies 22 open, expanding the spinal canal 20b. The stents 24 are slightly shorter in length than the osteotomies 22, preventing stent 24 projection into the expanded spinal canal 20b. The flange 50 abuts the edge of the osteotomy 22 at the base of the transverse process 14, preventing the stent 24 from sliding into the expanded spinal canal 20b. With the stent 24 in place, the interior section 52 of the stent 24 can be filled with bone graft material which assists in healing each osteotomy 22.

Figure 9C:
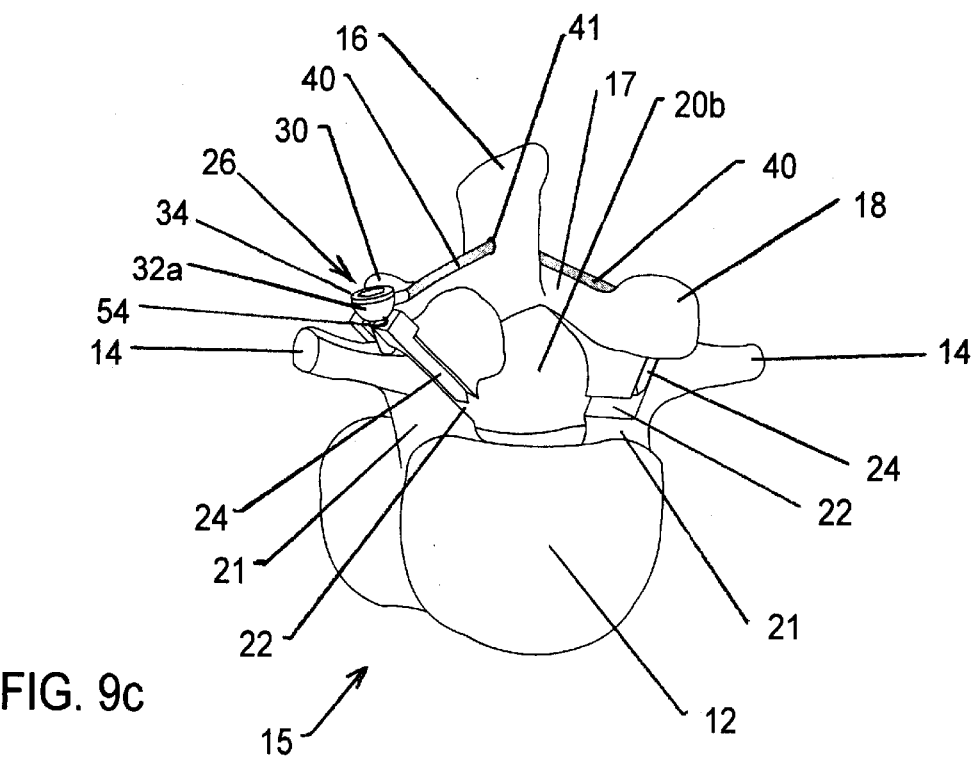
FIG. 9c illustrates a perspective view of the vertebra of FIG. 9b, with screws, rounded washers and a cable stabilizing the expanded spinal canal, in accordance with the present invention.

FIG. 9c illustrates the vertebra 15 of FIGS. 9a and 9b with the expanded spinal canal 20b after placement of the screws 26, the rounded washers 32a, 32b (the rounded washer 32b is not visible) and the cable 40. The screws 26 are placed through the rounded washers 32a, 32b and are threaded into the bone of the pedicle 21. The rounded washer 32a is seated in the rounded depression 54 of the stent 24, preventing the stent 24 from backing out of (or moving side to side in) the osteotomy 22. The rounded washer 32a is attached to the cable 40, the cable 40 is strapped around (lies on) each lamina 17 and passes through a hole 41 in the base of the spinous process 16. Alternatively, the cable 40 can be strapped around (instead of through) the spinous process 16. The cable 40 is tensioned and secured to the rounded washer 32b on the opposite side (not shown). The screws 26, the rounded washers 32a, 32b and the cable 40 secure the vertebra 15 during healing of the osteotomy 22.

Figure 10:
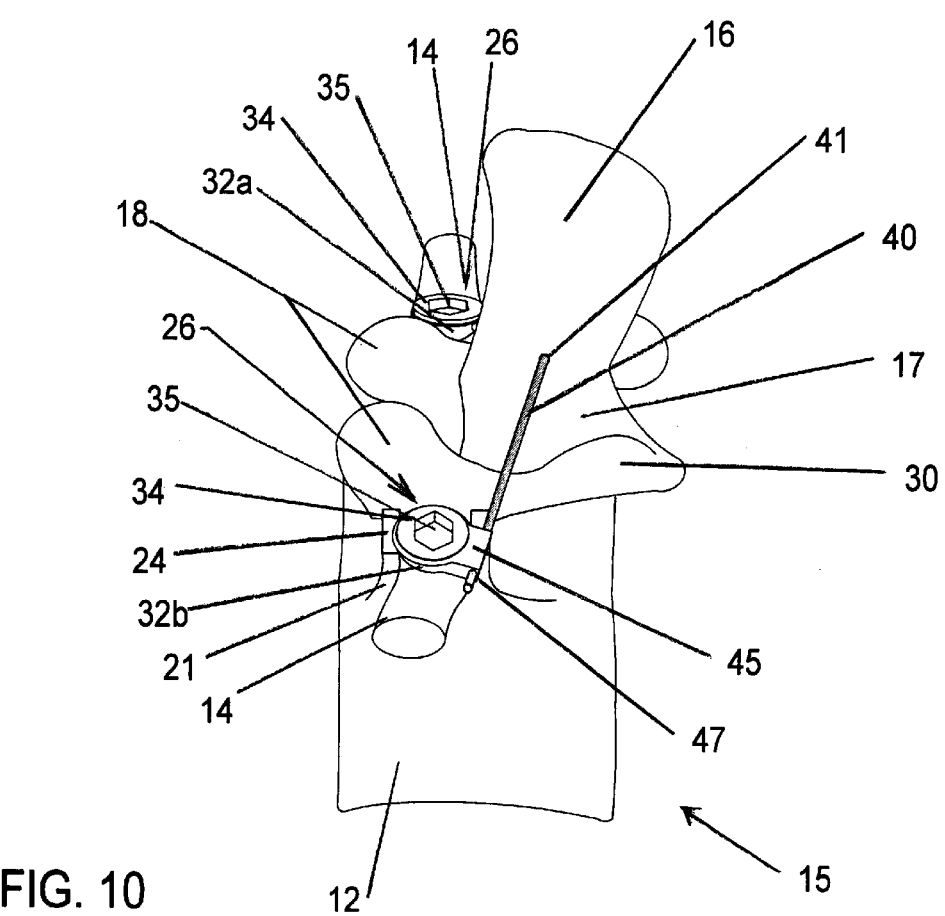
FIG. 10 illustrates a perspective view of the vertebra of FIG. 9a, viewed from the top right side, showing the relationship of the screw, a rounded washer with a side-attachment and the cable, in accordance with the present invention.

FIG. 10 illustrates a perspective view of the vertebra 15 of FIG. 9c from the upper right side, showing the head 34 of the screw 26, the rounded washer with side-attachment 32b, the stent 24 and the cable 40. The cable 40 passes over the lamina 17 after passing and through the hole 41 in the base of the spinous process 16. The rounded washer 32b includes a side passage 45 having a tunnel 47 slidably receiving the cable 40. The side passage 45 of the rounded washer 32b allows the cable 40 to be tensioned (remove slack) prior to attachment of the cable 40 to the rounded washer 32b. After the cable 40 is pulled taut through the tunnel 47, the side passage 45 is crushed or plastically deformed around the cable 40, fixedly securing the cable 40 to the rounded washer 32b.

In operation, one aspect of the method for expanding a spinal canal can be summarized as follows (referring to FIGS. 1–10): oblique osteotomies 22 are made through both pedicles 21 (FIGS. 5, 9a); the stents 24 are impacted into the osteotomies 22, opening the osteotomies 22 and expanding the spinal canal 20b (FIGS. 6, 9a, 9b); bone graft material is placed into the interior section 52 of the stent 24 to assist with healing (FIGS. 1, 6, 9b); the screws 26 are placed through the rounded washers 32a, 32b and the stents 24, the screws 26 are then threaded into the pedicles 21 to secure to stents 24 in place; a rounded washer with end-attachment 32a for the cable 40 may be used at one osteotomy 22, while a rounded washer with side-attachment 32b for the cable 40 is used at the second osteotomy 22 (FIGS. 1, 2, 3, 4, 8, 9c, 10); the cable 40 is passed through a hole 41 drilled through a base of the spinous process 16 (FIGS. 8, 9c, 10); the cable 40 is passed through the tunnel 47 in the side passage 45 of the rounded washer with side-attachment 32b, the cable 40 is then tensioned to remove all slack (FIGS. 8, 9c, 10); and the side passage 45 of the rounded washer 32b is crushed or plastically deformed to fixedly secure the cable 40 in place.

These and other advantages of the present invention will be apparent to those skilled in the art from the foregoing specification. Accordingly, it will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention.

What is claimed is:

1. A method for expanding a spinal canal, comprising:
   a. cutting a vertebra through to the spinal canal in at least one location;
   b. separating each vertebral cut to expand the spinal canal;
   c. securing each separated vertebral cut to allow the vertebra to heal with the spinal canal expanded.

2. The method of claim 1, wherein the vertebra is cut through the pedicle.

3. The method of claim 1, wherein the vertebral cut is separated by inserting an implant into the vertebral cut.

4. The method of claim 3, wherein the implant includes a stent and a screw, the stent separates the vertebral cut and the screw secures the stent and the separated vertebral cut.

5. The method of claim 4, wherein the stent is U-shaped having an interior section adapted to accept bone graft material to facilitate healing of the vertebral cut.

6. The method of claim 4, wherein the stent includes a rounded, wedge-shaped end for separating the vertebral cut.

7. The method of claim 4, wherein the stent includes a flange to prevent the stent from entering the spinal canal.

8. The method of claim 4, wherein the stent includes a rounded depression and the screw includes a rounded head, the rounded depression being adapted to rotatably accept the rounded head.

9. The method of claim 4, wherein the screw includes self-tapping, bone gripping threads for inserting the screw into the vertebra.

10. A method for expanding a spinal canal, comprising:
    a. cutting a vertebra in two locations, one cut through each pedicle of the vertebra, beginning at a base of a transverse process of the vertebra and coursing medially and anteriorly through the pedicle to the spinal canal;
    b. separating each vertebral cut by impacting a stent into each vertebral cut, whereby the spinal canal is expanded;
    c. securing each separated vertebral cut by inserting a screw through a washer and the stent and threading the screw into an anterior portion of the vertebra; and
    d. securing a posterior portion of the vertebra to the anterior portion of the vertebra by strapping a cable around the posterior portion of the vertebra, the cable being attached to a washer at each of its two ends.

11. The method of claim 10, wherein the screw includes a rounded head, the washer includes a rounded shape and the stent includes a rounded depression, the rounded washer engagably accepting the rounded head of the screw and rotatably residing within the rounded depression in the stent.

12. The method of claim 10, wherein at least one of the washers includes a crushable side-passage allowing slidable insertion of the cable through the side-passage, taut tensioning of the cable and permanent fixation of the cable to the washer by crushing the side-passage.

13. The method of claim 10, wherein the cable secures the posterior portion of the vertebra by lying over laminae of the vertebra and passing through a hole in a spinous process of the vertebra.

14. The method of claim 10, wherein the cable secures the posterior portion of the vertebra by lying over laminae of the vertebra and around a spinous process of the vertebra.

15. An implant for expanding a spinal canal, comprising:
    a. a stent for insertion into a cut in the vertebra to expand the spinal canal; and
    b. a screw inserted through the stent and threaded into the vertebra to secure the stent within the cut in the vertebra.

16. The implant of claim 15, wherein the stent includes a rounded, wedge-shaped end for inserting the stent into the cut in the vertebra.

17. The implant of claim 15, wherein the stent is U-shaped with an interior section adapted to accept bone graft material to facilitate healing of the cut in the vertebra.

18. The implant of claim 15, wherein the stent includes a flange limiting the distance the stent can be inserted into the cut in the vertebra, the flange preventing the stent from penetrating the spinal canal.

19. The implant of claim 17, wherein the stent includes a rounded depression and the screw includes a rounded head, the rounded head rotatably residing within the rounded depression.

20. An implant for expanding a spinal canal, comprising:
    a. two stents, one stent inserted into each of two cuts in the vertebra, each inserted stent expanding the spinal canal;
    b. two washers, one washer attached to each of two ends of a cable; and
    c. two screws, one screw inserted through one washer and one stent, each screw being threaded into an anterior portion of the vertebra to secure one washer and one stent to the anterior portion of the vertebra, with the cable strapped around a posterior portion of the vertebra to secure the posterior portion of the vertebra to the anterior portion of the vertebra to stabilize the expanded spinal canal.

21. The implant of claim 20, wherein the stents include a rounded depression, the washers include a rounded shape and the screws include a rounded head, the rounded head residing within the rounded washer and the rounded washer rotatably residing within the rounded depression.

22. The implant of claim 20, wherein at least one washer includes a crushable sidepassage for slidably accepting the cable therethrough, adjusting the cable tension and fixedly securing the cable to the washer by crushing the sidepassage.

23. The implant of claim 20, wherein the cable additionally passes through a hole in a spinous process of the vertebra to further secure the posterior portion of the vertebra to the anterior portion of the vertebra.

24. The implant of claim 20, wherein each stent includes a rounded, wedge-shaped end for inserting the stent into the cut in the vertebra.

25. The implant of claim 20, wherein each stent is U-shaped with an interior section adapted to accept bone graft material to facilitate healing of the cuts in the vertebra.

26. The implant of claim 20, wherein each stent includes a flange limiting the distance the stent can be inserted into the cut in the vertebra, the flange preventing the stent from penetrating the spinal canal.

* * * * *